United States Patent
Gutsche et al.

(10) Patent No.: US 7,084,313 B2
(45) Date of Patent: Aug. 1, 2006

(54) THREE STAGE PROCESSES FOR THE SEPARATION OF SUPERCRITICAL OR NEAR-CRITICAL MIXTURES

(75) Inventors: Bernhard Gutsche, Hilden (DE); Wilhelm Johannisbauer, Erkrath (DE); Harald Roessler, Duesseldorf (DE); Magnus Topphoff, Duesseldorf (DE)

(73) Assignee: Cognis Deutschland GmbH & Co. KG, Duesseldorf (DE)

(*) Notice: Subject to any disclaimer, the term of this patent is extended or adjusted under 35 U.S.C. 154(b) by 88 days.

(21) Appl. No.: 10/511,039

(22) PCT Filed: Apr. 2, 2003

(86) PCT No.: PCT/EP03/03433
§ 371 (c)(1),
(2), (4) Date: Oct. 12, 2004

(87) PCT Pub. No.: WO03/084907
PCT Pub. Date: Oct. 16, 2003

(65) Prior Publication Data
US 2005/0150380 A1 Jul. 14, 2005

(30) Foreign Application Priority Data
Apr. 11, 2002 (DE) ................. 102 15 862

(51) Int. Cl.
*C07C 27/04* (2006.01)
(52) U.S. Cl. ............... 568/885; 568/864; 568/913
(58) Field of Classification Search ................ 568/885, 568/864, 913
See application file for complete search history.

(56) References Cited

U.S. PATENT DOCUMENTS

| 4,568,653 A | 2/1986 | Schwirten et al. |
| 4,714,791 A | 12/1987 | Inada et al. |
| 5,734,070 A | 3/1998 | Tacke et al. |
| 5,962,711 A * | 10/1999 | Harrod et al. ............. 554/145 |
| 6,156,933 A * | 12/2000 | Poliakoff et al. .......... 564/416 |

FOREIGN PATENT DOCUMENTS

| EP | 0 791 041 B1 | 4/2001 |
| JP | 60 214757 A | 10/1985 |
| WO | WO 95/22591 A1 | 8/1995 |

OTHER PUBLICATIONS

"Supercritical, Single-Phase Hydrogenation Speeds Up The Production Of Fatty Alcohols," Chemical Engineering News, (Dec., 2001), p. 17.

* cited by examiner

Primary Examiner—Michael L. Shippen
(74) Attorney, Agent, or Firm—John F. Daniels

(57) ABSTRACT

Processes for separating supercritical or near-critical mixtures containing hydrogen, a solvent gas, methanol and a fatty alcohol under an initial pressure of from 100 to 300 bar are described, wherein the processes comprise: (a) reducing the pressure of such a mixture in a first stage to a pressure of from 50 to 150 bar to form a first recycle gas and a first partially-separated intermediate mixture, wherein the reduced pressure in the first stage is at least below the initial pressure; (b) reducing the pressure of the first partially-separated intermediate mixture in a second stage to a pressure of from 10 to 50 bar to form a second recycle gas and a second partially-separated intermediate mixture; and (c) reducing the pressure of the second partially-separated intermediate mixture in a third stage to a pressure of from 1 to 10 bar to form a third recycle gas and a fatty alcohol product.

20 Claims, 1 Drawing Sheet

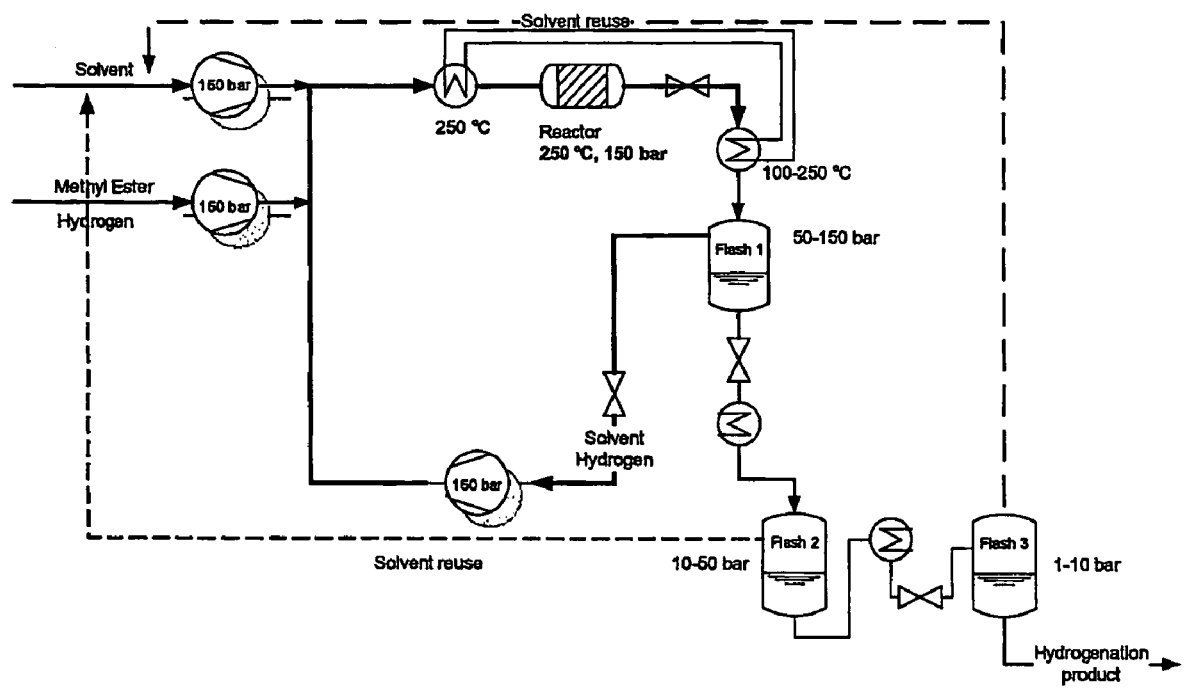

THREE STAGE PROCESSES FOR THE SEPARATION OF SUPERCRITICAL OR NEAR-CRITICAL MIXTURES

BACKGROUND OF THE INVENTION

Prior Art

According to the prior art, fatty alcohols are conventionally produced by catalytic hydrogenation of the corresponding methyl esters in the absence of a solvent. However, hydrogenation in the presence of a solvent in the supercritical or near-critical single-phase range offers the advantage of a faster reaction. Thus, European patent EP 0 791 041 B1 describes the hydrogenation of fatty acid methyl esters to fatty alcohols in the presence of propane to establish a supercritical state. The advantage of this procedure lies in the production of a homogeneous phase in contrast to the traditional, industrially practised process in a trickle-bed reactor with two liquid phases. By creating a fluid phase, it is possible to obtain far higher volume/time yields. However, the supercritical mixture consisting of hydrogen, propane, methanol and fatty alcohol has to be separated. In the cited document, there is no recycling of the hydrogen or the propane which are therefore lost and make the process unprofitable. In Chem. Eng. News 2001 December, page 17, Härröd proposes for the first time for such a process the separation of hydrogen and propane in a column and their recycling as recycle gases after expansion, i.e. removal of the reaction conditions of 250° C./150 bar. However, the conditions for the pressure stages are not mentioned even though they are critical to any economic evaluation and determine whether or not the process is viable.

Accordingly, the problem addressed by the present invention was to find a way of separating the compressed gas mixtures acumulating in a process for the supercritical or near-critical hydrogenation of fatty acid methyl esters to the corresponding fatty alcohols with minimal outlay on equipment and under optimal economic conditions without reducing the quality and particularly the purity of the fatty alcohols obtained.

BRIEF SUMMARY OF THE INVENTION

The present invention relates, in general, to the production of fatty alcohols, especially by hydrogenation of the corresponding esters under supercritical or near-critical conditions, and more particularly to a technically simplified and economically optimized process for separating the compressed gas mixtures.

The invention is based on the observation that expansion should be carried out in three stages and the pressure difference between the reaction pressure and the pressure level of the expansion process should be minimal to keep the recompression costs to a minimum. On the other hand, however, separation of the fatty alcohol and the methanol from the hydrogen/inert gas mixture must be guaranteed. By analyzing the cost of recycling hydrogen/inert gas at different pressure and temperature levels of the pressure stages, it was possible to find an optimum in regard to outlay on equipment and process costs.

DETAILED DESCRIPTION OF THE INVENTION

Operation of the Process

The hydrogenation of a substrate is normally carried out in the presence of a solvent, preferably propane, in the supercritical or near-critical range. In contrast to other words, expansion in the first stage ("flash") takes place to a pressure of 50 to 150 bar. This has proved to be advantageous for minimizing the compression costs of the process as a whole. Under the effect of the phase equilibrium taken as a basis, the fatty alcohol and the methanol are completely separated from the reaction mixture, the lower the pressure and the higher the temperature. The separation of the fatty alcohol should be complete under the conditions applied whereas the separation of the methanol can be partial because a methanol content of up to at most 5% in the recycle gas is not problematical to the process. The pressure in the first separation stage should be near the reaction pressure in order to avoid cost-intensive compression of the main quantity of recycled solvent and excess hydrogen. Even with an expansion to 10 bar in the first separation stage, the process as a whole can otherwise become unprofitable in consequence of the resulting compression costs. In the following step-by-step expansion to the pressure stage between 10 and 50 and 1 and 10 bar, the solvent and the methanol are separated off. The hydrogenation product is worked up. Other advantageous embodiments of the process comprise on the one hand recycling the inert gas with the excess hydrogen and, on the other hand, the recycled mixtures containing up to 5 mol-% methanol.

In addition, it has been found that the ratio between the educts is very important to the profitability of the process. In a particularly advantageous embodiment, the percentage content of the substrate is between 1 and 4 mol-% and more particularly ca. 2 mol-% and the pecentage of hydrogen is between 10 and 20 and more particularly between 12 and 18 mol-%. If the quantities of substrate used are too small (<1 mol-%), the process becomes unprofitable in view of the large excess of inert gas/hydrogen for a given quantity of fatty alcohol to be produced. For example, for the production of 20,000 t/a fatty alcohol, 9300 kg/h propane are required for a ratio of propane to hydrogen to fatty acid methyl ester of 85:12:3 mol-%. With a ratio of 200:60:1, however, 74,000 kg/h propane has to be compressed and recycled to produce the same quantity of fatty alcohol. This means that, for an economic process, the quantity of substrate should be as large as possible in order to minimize the quantity of propane to be recycled.

With regard to the quantity of hydrogen to be used, calculation of the thermodynamic parameters has shown that an increase in the percentage content of hydrogen in the starting mixture facilitates separation of the fatty alcohol in the first pressure stage. Accordingly, the solubility of the fatty alcohol in the propane/hydrogen mixture decreases with increasing hydrogen content. Accordingly, a percentage hydrogen content of 10 to 20 mol-% is particularly advantageous for complete separation of the fatty alcohol from the reaction mixture.

EXAMPLES

In a plant for the hydrogenation of fatty acid methyl esters as describd in EP 0 791 041 B1, coconut oil fatty acid methyl ester was hydrogenated at 250° C./150 bar in the presence of a commercially available copper/zinc catalyst to form the corresponding fatty alcohol. A flow chart of the plant is shown in FIG. 1. The ratio of propane to hydrogen to methyl ester was 85:12:3 parts by weight. Assuming a running time of 8,000 h/a, the energy consumption for the necessary compression and the loss of propane were calculated for various expansion stages. The results are set out in Table 1. Examples 1 and 2 correspond to the invention, Example C1 is intended for comparison.

TABLE 1

Energy consumption and loss of propane

| Example | Pressure stages [bar] | Energy consumption [MW/a] | Loss of propane [kg/a] |
|---------|----------------------|---------------------------|------------------------|
| 1 | 1st stage: 100 bar<br>2nd stage: 10 bar<br>3rd stage: 1 bar | 2,541 | 344,000 |
| 2 | 1st stage: 50 bar<br>2nd stage: 10 bar<br>3rd stage: 1 bar | 2,222 | 416,000 |
| C1 | 1st stage: 10 bar<br>2nd stage: 1 bar | 10,224 | 120,000 |

The results show that far less energy is required for recompression in the process according to the invention, even though the losses of inert gas are considerably higher. However, if it is taken into account that the cost of 100 kWh energy is on average 10 times higher than the price of 1 kg propane, it can clearly be seen that the process according to the invention operates far more favorably in regard to its economic conditions.

The invention claimed is:

1. A process for separating a supercritical or near-critical mixture which comprises hydrogen, a solvent gas, methanol and a fatty alcohol under an initial pressure of from 100 to 300 bar, said process comprising:
   (a) reducing the pressure of the mixture in a first stage to a pressure of from 50 to 150 bar to form a first recycle gas and a first partially-separated intermediate mixture, wherein the reduced pressure in the first stage is at least below the initial pressure;
   (b) reducing the pressure of the first partially-separated intermediate mixture in a second stage to a pressure of from 10 to 50 bar to form a second recycle gas and a second partially-separated intermediate mixture; and
   (c) reducing the pressure of the second partially-separated intermediate mixture in a third stage to a pressure of from 1 to 10 bar to form a third recycle gas and a fatty alcohol product.

2. The process according to claim 1, wherein the supercritical or near-critical mixture is a product of fatty acid methyl ester hydrogenation for the production of fatty alcohols.

3. The process according to claim 1, wherein the solvent gas comprises propane.

4. The process according to claim 2, wherein the solvent gas comprises propane.

5. The process according to claim 1, wherein the supercritical or near-critical mixture comprises a fatty alcohol in an amount of from 1 to 4 mole percent.

6. The process according to claim 2, wherein the supercritical or near-critical mixture comprises a fatty alcohol in an amount of from 1 to 4 mole percent.

7. The process according to claim 3, wherein the supercritical or near-critical mixture comprises a fatty alcohol in an amount of from 1 to 4 mole percent.

8. The process according to claim 1, wherein the supercritical or near-critical mixture comprises hydrogen in an amount of from 10 to 20 mole percent.

9. The process according to claim 2, wherein the supercritical or near-critical mixture comprises hydrogen in an amount of from 10 to 20 mole percent.

10. The process according to claim 3, wherein the supercritical or near-critical mixture comprises hydrogen in an amount of from 10 to 20 mole percent.

11. The process according to claim 5, wherein the supercritical or near-critical mixture comprises hydrogen in an amount of from 10 to 20 mole percent.

12. The process according to claim 1, wherein one or more of the first, second and third recycle gases comprises a portion of the solvent gas and excess hydrogen.

13. The process according to claim 1, wherein one or more of the first, second and third recycle gases comprises methanol in an amount of up to 5 mole percent.

14. The process according to claim 12, wherein one or more of the first, second and third recycle gases comprises methanol in an amount of up to 5 mole percent.

15. The process according to claim 2, wherein one or more of the first, second and third recycle gases comprises a portion of the solvent gas and excess hydrogen.

16. The process according to claim 2, wherein one or more of the first, second and third recycle gases comprises methanol in an amount of up to 5 mole percent.

17. The process according to claim 15, wherein one or more of the first, second and third recycle gases comprises methanol in an amount of up to 5 mole percent.

18. The process according to claim 3, wherein one or more of the first, second and third recycle gases comprises a portion of the solvent gas and excess hydrogen.

19. The process according to claim 3, wherein one or more of the first, second and third recycle gases comprises methanol in an amount of up to 5 mole percent.

20. The process according to claim 18, wherein one or more of the first, second and third recycle gases comprises methanol in an amount of up to 5 mole percent.

* * * * *